United States Patent
Voellmicke et al.

(10) Patent No.: US 7,156,803 B2
(45) Date of Patent: Jan. 2, 2007

(54) DEVICES FOR CONTROLLING FLUID FLOW THROUGH A MEDIUM

(75) Inventors: John C. Voellmicke, Cumberland, RI (US); Mathew Parsons, Fall River, MA (US); Nicholas Catalano, Cumberland, RI (US); Randa Bobroff, Braintree, MA (US)

(73) Assignee: DePuy Spine, Inc., Raynham, MA (US)

( * ) Notice: Subject to any disclaimer, the term of this patent is extended or adjusted under 35 U.S.C. 154(b) by 711 days.

(21) Appl. No.: 10/223,674

(22) Filed: Aug. 19, 2002

(65) Prior Publication Data

US 2004/0034276 A1    Feb. 19, 2004

(51) Int. Cl.
A61F 2/00     (2006.01)

(52) U.S. Cl. ........................................... 600/36
(58) Field of Classification Search .................. 600/36; 128/897, 898; 435/1.2, 284.1
See application file for complete search history.

(56) References Cited

U.S. PATENT DOCUMENTS

| | | | |
|---|---|---|---|
| 2,705,494 A | 4/1955 | Broadwin | |
| 3,596,652 A | 8/1971 | Winkelman | |
| 4,381,006 A | 4/1983 | Genese | |
| 4,417,861 A * | 11/1983 | Tolbert | 417/315 |
| 4,557,728 A | 12/1985 | Sealfon et al. | |
| 4,564,359 A | 1/1986 | Ruhland | |
| 4,664,128 A | 5/1987 | Lee | |
| 4,755,172 A | 7/1988 | Baldwin | |
| 4,777,137 A * | 10/1988 | Lemonnier | 435/288.1 |
| 4,795,467 A | 1/1989 | Piez et al. | |
| 4,992,226 A | 2/1991 | Piez et al. | |
| 5,014,715 A * | 5/1991 | Chapolini | 600/485 |
| 5,040,678 A | 8/1991 | Lenmark, Sr. et al. | |
| 5,159,933 A | 11/1992 | Hut | |
| 5,187,095 A * | 2/1993 | Bliem et al. | 435/299.1 |
| 5,240,861 A | 8/1993 | Bieri | |
| 5,298,020 A | 3/1994 | Stone | |
| 5,354,468 A | 10/1994 | Richards | |
| 5,395,345 A | 3/1995 | Gross | |
| 5,431,649 A | 7/1995 | Mulier et al. | |
| 5,549,816 A | 8/1996 | Harp et al. | |
| 5,762,071 A * | 6/1998 | Newman et al. | 600/573 |
| 5,792,603 A * | 8/1998 | Dunkelman et al. | 435/1.2 |
| 5,800,374 A | 9/1998 | Beyersdorf | |
| 5,800,702 A | 9/1998 | Taylor-McCune et al. | |
| 6,033,911 A | 3/2000 | Schultz et al. | |
| 6,049,026 A | 4/2000 | Muschler | |
| 6,060,306 A * | 5/2000 | Flatt et al. | 435/297.2 |
| 6,135,320 A | 10/2000 | Parsons | |
| 6,143,019 A | 11/2000 | Motamedi et al. | |

(Continued)

FOREIGN PATENT DOCUMENTS

DE     196 53 325 A1    6/1998

(Continued)

*Primary Examiner*—Samuel G. Gilbert
(74) *Attorney, Agent, or Firm*—Nutter, McClennen & Fish LLP

(57) ABSTRACT

A fluid flow system for preparing an implantable substrate is provided having a fluid permeable container that is capable of retaining a biocompatible, implantable substrate, and a driver mechanism for subjecting fluid to a constant force to induce a selected, controlled flow rate of the fluid through a substrate disposed in the container. The system can include a fluid reservoir having an inlet and an outlet, and being effective to selectively retain a fluid. The reservoir is preferably disposed upstream of the container. The system can also optionally include a fluid recycling conduit that is effective to recirculate fluid from the container to the reservoir.

40 Claims, 13 Drawing Sheets

U.S. PATENT DOCUMENTS

| | | |
|---|---|---|
| 6,153,104 A | 11/2000 | Robertson |
| 6,197,194 B1 | 3/2001 | Whitmore |
| 6,305,379 B1 | 10/2001 | Wolfinbarger, Jr. |
| 6,312,950 B1 | 11/2001 | Ohmura et al. |
| 6,355,174 B1 | 3/2002 | Robertson |
| 6,416,995 B1 * | 7/2002 | Wolfinbarger ............ 435/289.1 |
| 2002/0049405 A1 | 4/2002 | Deslauriers et al. |

FOREIGN PATENT DOCUMENTS

| | | |
|---|---|---|
| JP | 3-60501 B | 9/1991 |
| JP | 8-301775 | 11/1996 |
| WO | WO-01/47571 | 7/2001 |

* cited by examiner

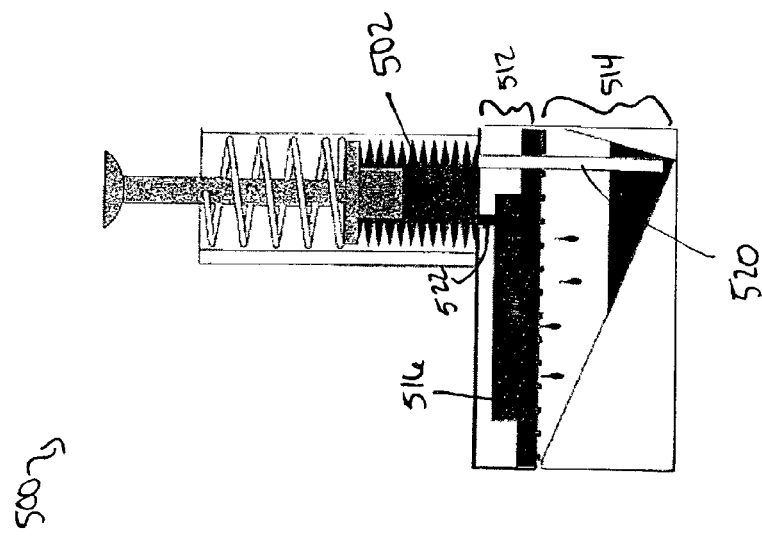
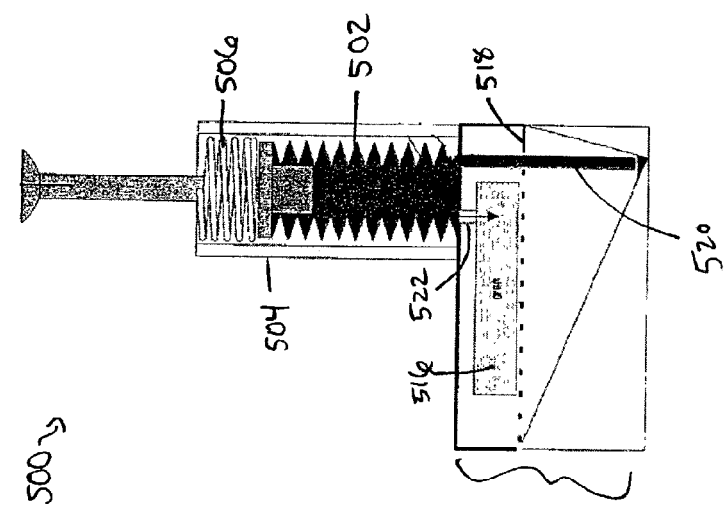
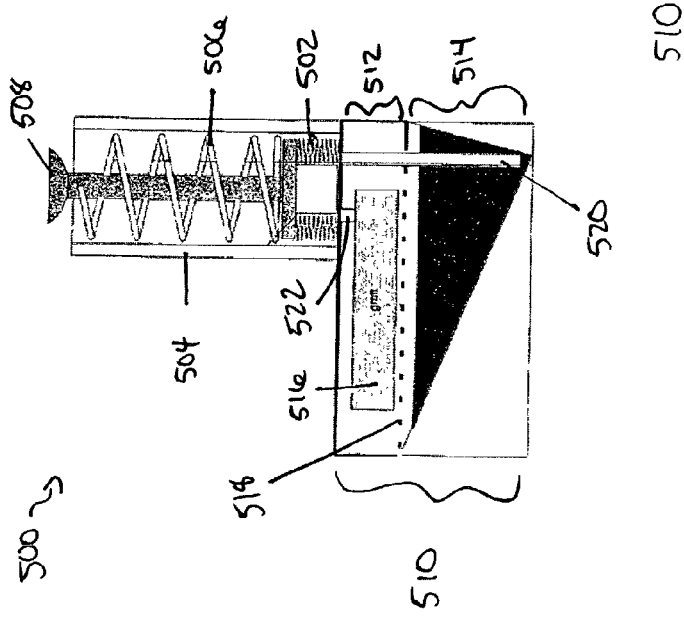

DEVICES FOR CONTROLLING FLUID FLOW THROUGH A MEDIUM

FIELD OF THE INVENTION

The present invention relates to devices and systems for preparing an implantable substrate, and in particular to devices and systems for directing fluid through an implantable substrate, such as a bone graft.

BACKGROUND OF THE INVENTION

Bone grafts are often used to treat fractures, gaps in bones caused by trauma or infection, revision joint surgery, and oral/maxillofacial surgery. Bone grafts provide a framework into which the host bone can regenerate and heal. Once implanted, the bone cells weave into and through the porous microstructure of the bone graft to support the new tissue, blood cells and soft tissue as they grow to connect fractured bone segments.

Bone grafts can be prepared from a variety of materials, including bone harvested from a patient. Bone harvesting procedures, however, can result in significant cost and morbidity, including scars, blood loss, pain, prolonged operative and rehabilitation time and risk of infection. Furthermore, in some clinical settings, the volume of the graft site can exceed the volume of the available autograft. Accordingly, alternatives to autografts have been developed in an attempt to reduce the morbidity and cost of bone grafting procedures. Such alternative materials include purified or synthetic materials, such as ceramics, biopolymers, processed allograft bone and collagen-based matrices. These materials are typically used as carriers for bone marrow cells, and thus need to be prepared prior to implantation.

U.S. Pat. Nos. 5,824,084 and 6,049,026 disclose apparatus and methods for preparing implantable bone grafts having an enriched population of connective tissue progenitor cells. By infusing certain biologically active cells into a bone graft, it was found that the rate and quality of new bone formation is significantly improved. The bone grafts are prepared by flushing aspirated bone marrow one or more times to collect and concentrate the stem cells contained in the marrow into a bone matrix. While this procedure can be very effective, it can also be time consuming typically requiring around 20 minutes for the aspiration procedure, and an additional 20 minutes for the matrix preparation procedure.

Accordingly, there is a need for more efficient and effective methods and devices for preparing implantable substrates.

SUMMARY OF THE INVENTION

In general, the present invention provides a system for preparing a bone graft for implantation having a reservoir including an inlet and an outlet, a container coupled to the reservoir and having an inlet and an outlet, and a driver mechanism coupled to the container and the reservoir. The reservoir is preferably capable of selectively retaining a fluid, and the container is preferably fluid permeable, but capable of retaining a porous, biocompatible, implantable substrate. In use, the driver mechanism is effective to subject any fluid within the reservoir to a constant force so as to induce a selected, controlled flow rate of the fluid through the container. The system can also optionally include a fluid recycling conduit extending between the outlet of the container and the inlet of the reservoir to recirculate the fluid to the reservoir. The fluid recycling conduit can include a one-way check valve to prevent any fluid from entering the container through the outlet thereof. In an exemplary embodiment, at least one of the reservoir, the container, and the driver mechanism are disposed within a housing.

The container can have a variety of configurations. In one embodiment, the container is a tray-like device having a porous bottom surface, a porous top surface, and at least one non-porous sidewall. The driver mechanism used with the system can also have a variety of configurations. In one embodiment, the driver mechanism is formed from one or more syringes that are effective to create a constant suction force to transport fluid through the container. Each syringe preferably includes a barrel and a plunger disposed within the barrel. The plunger is preferably coupled to a constant force spring that is effective to retract the plunger from an initial position, in which the plunger is substantially disposed within the barrel, and a final position, in which the plunger is substantially retracted from the barrel. In use, the syringe(s) are effective to create a constant pressure differential on fluid in the reservoir to transport the fluid from the reservoir through the container, or through the container to the reservoir, depending on the configuration of the system. In an exemplary embodiment, the plunger is biased to a position in which the plunger is substantially fully retracted from the barrel.

In another embodiment, the system includes a collection tank effective to collect fluid from the outlet of the container, and a fluid recycling conduit extending between the collection tank and the inlet of the reservoir. A withdrawal conduit can extend between the fluid recycling conduit and the driver mechanism.

In another embodiment, the driver mechanism includes a bellows movable between expanded and compressed positions. In this embodiment, the reservoir is preferably disposed downstream of the container such that fluid flows from the outlet of the container to the inlet in the reservoir. Thus, the bellows is effective to collect fluid from the outlet in the reservoir and to deliver fluid to the inlet in the container. The system can further include a first conduit extending between the inlet in the container and the bellows, and a second conduit extending between the outlet in the reservoir and the bellows. The first conduit can optionally include a one-way valve that is effective to permit fluid flow only in a direction from the bellows to the container, and the second conduit can include a one-way valve that is effective to permit fluid flow only in a direction from the reservoir to the bellows.

In further aspects, the system can include a plunger device that is adapted to apply a force to the bellows to transport fluid from the reservoir to bellows, and then from the bellows to the container as a result of expansion and contraction of the bellows. The plunger device is preferably coupled to a constant force spring which is effective to bias the plunger to one of a first position, in which the bellows is expanded, and a second position, in which the bellows is contracted. In one embodiment, the plunger is biased to the second position and movement of the plunger device in opposition to the biasing force of the constant force spring is effective to create a suction force to draw fluid from the reservoir into the bellows. The biasing force thereafter causes the bellows to contract to push fluid through the container. In another embodiment, the plunger is biased to the first position and movement of the plunger device in opposition to the biasing force of the constant force spring is effective to create a positive pressure to push fluid through the reservoir. The biasing force thereafter causes the bellows to expand to draw fluid from the container into the bellows.

In another embodiment, a system for preparing a bone graft for implantation is provided having first and second vertically oriented bellows, each having an open end and a closed end, a fluid permeable container disposed between the first and second bellows such that the container is in fluid communication with the open end of each of the first and second bellows, and a driver mechanism operatively coupled to the closed end of at least one of the first and second bellows. The driver mechanism is selectively engageable to apply a compressive force to one of the first or second bellows to enable any fluid within one of the first or second bellows to flow from the open end thereof through the container at a selected, controlled rate of flow. The system can also include a flow control device disposed between at least one of the first and second bellows and the container. The flow control device can be effective to selectively control the flow rate of fluid flowing from one of the first and second bellows to the container, and to allow fluid to flow freely from the container to one of the first and second bellows. The system can also optionally include a housing that encompasses the first bellows, the second bellows, the container, and the driver mechanism. The housing is preferably substantially hollow to allow expansion and compression of the first and second bellows.

In yet another embodiment, a system for preparing an implantable, biological substrate is provided having a chamber including a first end having an inlet, a second end having an outlet, and at least one sidewall extending between the first and second ends, a basket disposed within the chamber between the first and second ends and capable of retaining an implantable substrate and allowing fluid to flow therethrough, and a driver mechanism coupled to at least one of the inlet port and outlet port of the chamber. The driver mechanism is effective to drive fluid, at a substantially constant flow rate, through an implantable substrate disposed within the basket. In an exemplary embodiment, the basket includes first and second porous, substantially planar members disposed at a distance apart from one another and effective to retain an implantable substrate therebetween. The system can also include a recycling conduit extending between the fluid inlet and the fluid outlet, such that fluid can be recycled through the chamber.

The present invention also provides a container for holding an implantable substrate. The container includes a fluid retaining member having a longitudinal axis, a proximal end, a distal end, and at least one fluid impermeable sidewall defining a substantially hollow interior portion, and a base member mated to and extending in a direction substantially transverse to the longitudinal axis of the fluid retaining member. The base member has at least one porous portion adapted to allow fluid to flow therethrough. The container further includes a first lid member removably disposed within the hollow interior portion of the fluid retaining member, and a second lid member removably mated to the proximal end of the fluid retaining member. The first lid member is preferably positioned at about a midpoint in the hollow interior portion of the fluid retaining member, and extends in a direction substantially parallel to the base member. The lid member can include a handle and at least one porous portion adapted to allow fluid to flow therethrough. In a preferred embodiment, the first lid member is removably mated to the fluid retaining member by a positive mechanical engagement. In other aspects, the container can include a support member having a recess for removably receiving the fluid retaining member.

BRIEF DESCRIPTION OF THE DRAWINGS

The invention will be more fully understood from the following detailed description taken in conjunction with the accompanying drawings, in which:

FIGS. 7A–7C illustrate another embodiment of a fluid flow control system according to the present invention;

DETAILED DESCRIPTION OF THE INVENTION

The present invention generally provides a system for preparing an implantable substrate, such as a bone graft. The system is preferably used to direct fluid through an implantable substrate at a selected, controlled flow rate, thereby causing biologically active material present within the fluid to attach to the implantable substrate to provide an enriched substrate. The invention is particularly advantageous in that the use of a preselected, controlled flow rate will cause the biologically active materials present within the fluid to attach more readily to the implantable substrate when flowed through the substrate.

A person having ordinary skill in the art will appreciate that a variety of implantable substrates and fluid can be used with the system of the present invention. By way of non-limiting example, suitable implantable substrates include bone grafts, fusion cages, ceramic bone substitutes, soft tissue grafts, such as skin tendons, and ligaments, and other suitable implantable materials. Suitable fluids include, for example, fluids having regenerative properties, such as bone marrow, blood, platelet rich plasma, placenta, synovial fluid, and amniotic fluid, and suspensions containing stem cells, growth factors, and proteins.

The system of the present invention can have a variety of configurations, but preferably includes a container that is adapted to hold an implantable substrate, and a driver mechanism coupled to the container for directing fluid, preferably at a selected, controlled flow rate, through the implantable substrate disposed within the container. The container and driver mechanism can be formed as a single, integral unit, or alternatively can be formed as separate components coupled together. In use, the system can be connected to an outside fluid source, or alternatively fluid can be disposed within the system, and the system can then be sealed to allow a force to be applied to the fluid to move the fluid through the system.

While FIGS. 1–10C illustrate preferred embodiments of the present invention, a person having ordinary skill in the art will appreciate that adaptation and modifications can be made to the various embodiments disclosed without departing from the scope of the invention. By way of non-limiting example, the system can be modified to move an implantable substrate through a fluid source at a constant flow rate, rather than to flow fluid through an implantable substrate at a constant rate. Moreover, the various embodiments disclosed can be modified to include a variety of features present in other embodiments, and any combination of features disclosed can be used to provide a system in accordance with the present invention.

Figure 1:
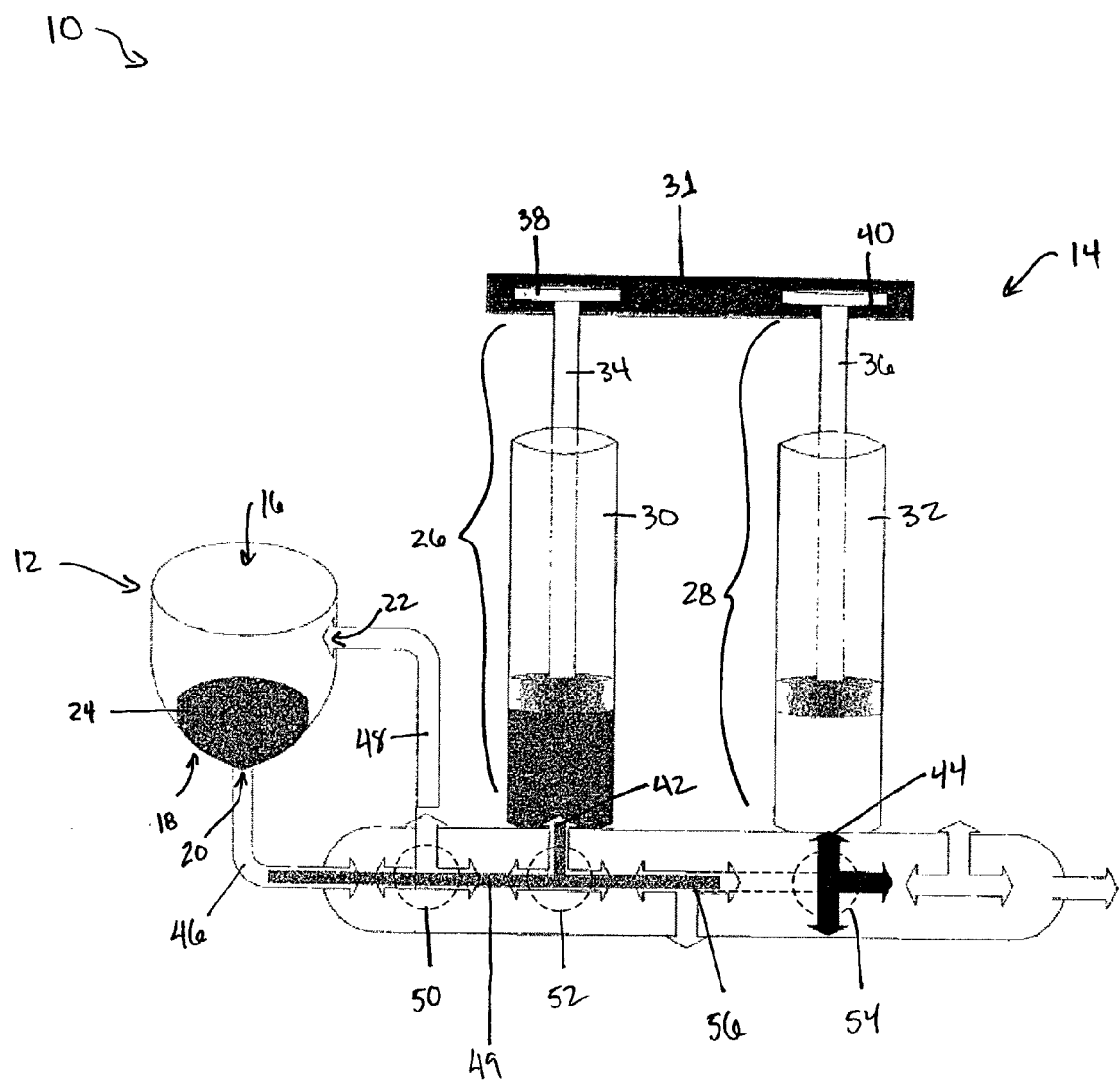
FIG. 1 is a functional diagram of a system according to one embodiment of the invention.

FIG. 1 illustrates a functional diagram of one embodiment of a system 10 according to the present invention. As shown, the system 10 includes a chamber or container 12 coupled to a driver mechanism 14 for driving fluid through the container 12. The container 12 and the driver mechanism 14 can have virtually any configuration, and various embodiments of a container and a driver mechanism for use with the present invention are shown in FIGS. 2A–4A, and 5A–5B, 7A–7C, 8B, and 9. A person having ordinary skill in the art will appreciate that the configuration of the container and the driver mechanism can significantly vary without departing from the scope of the invention.

While the container 12 can have virtually any shape and size, FIG. 1 illustrates a generally conical-shaped container 12 having a proximal end 16, a distal end 18, and a hollow interior forming a fluid reservoir for receiving and holding a biologically active fluid. The proximal end 16 of the container 12 preferably includes a central opening, and is adapted to receive a removable cover (not shown). An inlet 22 is formed adjacent to the proximal end 16 of the container 12, in the proximal end 16 of the container 12, or in the lid (not shown), and an outlet 20 is formed in or adjacent to the distal end 18 of the container 12. The inlet and outlets 22, 20 can have any shape and size and, by way of non-limiting example, can be in the form of a port or a valve. The container 12 further includes a basket 24 or similar structure disposed within the reservoir 22 for retaining an implantable substrate. The basket 24, or a portion of the basket 24, can be removably disposed within the container, or integrally formed with the container. The basket 24, or at least a portion of the basket 24, is fluid permeable to allow fluid to flow through an implantable substrate disposed therein. The basket 24 can have a variety of configurations, and various embodiments will be described in greater detail below.

Figure 2A:
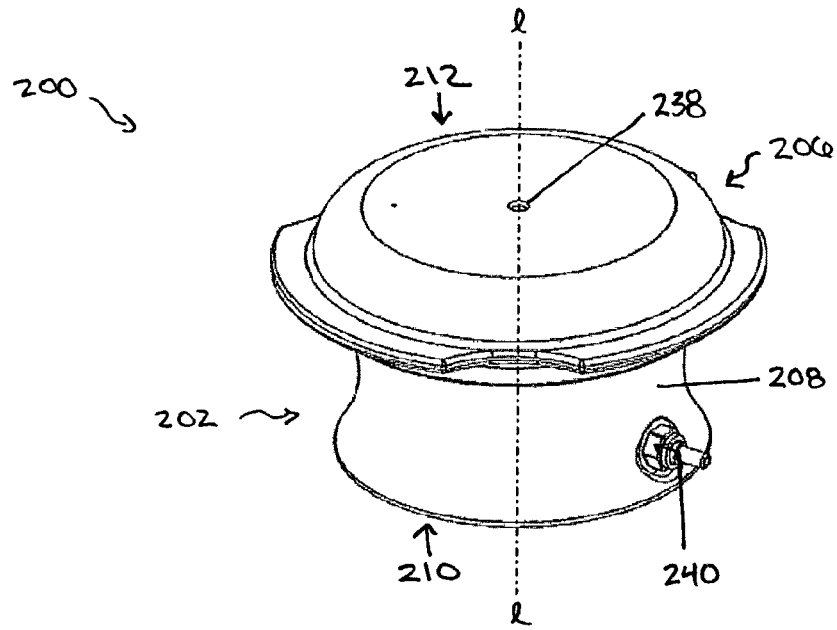
FIG. 2A is a perspective view of one embodiment of a container for use with a system according to the present invention.
Figure 2B:
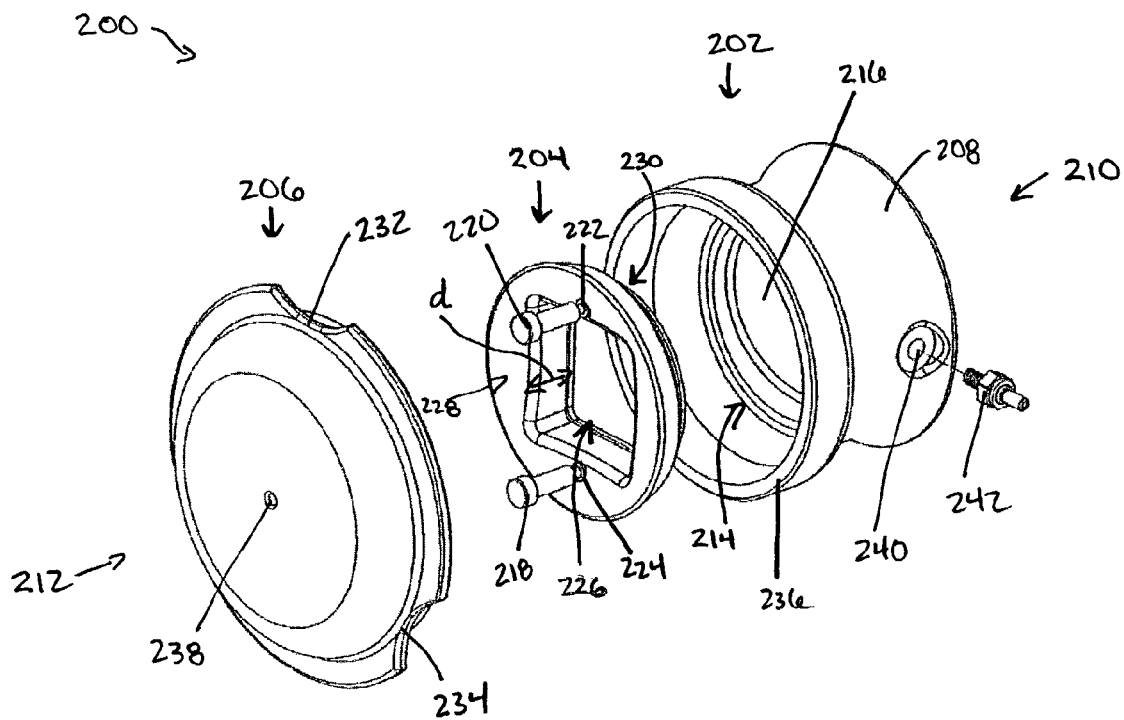
FIG. 2B is an exploded view of the container of FIG. 2A.

An exemplary embodiment of a container for use with the system 10 of FIG. 1 is shown in FIGS. 2A–2B. The container 200 includes a fluid retaining member 202, a first lid or basket 204 disposed within the fluid retaining member 202, and a second lid or cover 206 disposed on one end of the fluid retaining member 202. The fluid retaining member 202 can have virtually any shape, such as square, cylindrical, etc., and can have any size. As shown, the fluid retaining member 202 has a substantially cylindrical elongate shape having a longitudinal axis l, a proximal end 212, a distal end 210, and a sidewall 208 extending between the proximal and distal ends 212, 210. The sidewall 208 defines a substantially hollow interior 214, which preferably has a size and shape adapted to receive an implantable substrate, or a structure holding an implantable substrate. The distal end 210 of the fluid retaining member 202 preferably includes a base member 216 integrally formed with, removably attached to, or fixedly attached to the sidewall 208, and the proximal end 212 is preferably open to receive the basket 204.

The basket 204 can also have a variety of configurations, but should be adapted to retain an implantable substrate, and to allow fluid to flow therethrough. As shown in FIG. 2B, the basket 204 has a generally cylindrical shape that is sized to fit within the hollow interior 214 of the fluid retaining member 202. The basket 204 further includes a proximal end 228, a distal end 230, and a central opening 226 extending therethrough. The depth d of the basket 204 between the proximal and distal ends 228, 230 can vary, but should be sufficient to retain an implantable substrate, such as a bone graft. The central opening 226 in the basket 204 can have a variety of shapes, but preferably has the same shape as the implant desired to be prepared. The basket 204 further includes first and second porous members (not shown) disposed on and extending across opposed ends of the central opening 226 for allowing fluid to flow through the central opening 226 and the implantable substrate disposed therein. The porous members are preferably substantially planar members that are positioned parallel to and a distance apart from one another. The porous members can be formed from a variety of materials including, for example, mesh or woven screens, netting, and laser etched, die cut, or injection molded holes formed in a plastic or metal insert. The materials forming the porous members can optionally be biologically compatible to form part of the implantable substrate. Alternatively, the porous members can be integrally formed with the basket. In an exemplary embodiment, the porous member positioned on the distal end 230 of the opening 226 is integrally formed with, or fixedly mated to the basket 204, and the porous member on the proximal end 228 of the opening 226 is removably mated to the basket 204 to enable an implantable substrate to be disposed within the opening 226. The pores or apertures formed in each of the porous members can have any shape and size, but preferably have a size between about 175 and 600 microns.

The basket 204 can further include one or more mating elements for mating the basket 204 to the fluid retaining member 202. By way of non-limiting example, FIG. 2B illustrates first and second pin members 218, 220 that extend through first and second bores 222, 224 formed in the basket 204 to mate with corresponding bores (not shown) formed in the base 210 of the fluid retaining member 202. A person having ordinary skill in the art will appreciate that a variety of mating techniques can be used to mate the basket 204 to the fluid retaining member 202 including, for example, a snap-fit engagement, a magnetic engagement, an interference fit, and a threaded engagement.

The container 200 also includes a lid 206, shown in FIG. 2B, that is removably matable with the proximal end 212 of the fluid retaining member 202. The lid 206 can have any shape and size, but should be sized to seal the hollow interior 214 of the fluid retaining member 202. As shown in FIG. 2B, the lid 206 has a substantially cylindrical shape and includes first and second detents 232, 234 to facilitate grasping of the lid 206. The lid 206 can mate with a portion of the proximal end 212 of the fluid retaining member 202, such as a rim 236 formed on the proximal end 212, or alternatively the lid 206 can extend around the proximal portion 212 of the fluid retaining member 202. A variety of mating techniques can be used to mate the lid 206 to the fluid retaining member 202 including, for example, a snap-fit engagement, a magnetic engagement, an interference fit, and a threaded engagement. In an exemplary embodiment, the lid 206 is formed from a material having some elasticity to allow the lid 206 to be stretched to fit around the proximal portion 212 of the fluid retaining member 202.

The container 200 further includes an inlet 238 and an outlet 240. The inlet 238 and outlet 240 can be positioned anywhere on the container 200, but the inlet 238 should be positioned proximal to the basket 204, and the outlet 240 should be positioned distal to the basket 204. FIG. 2B illustrates one embodiment in which the inlet 238 is formed in the lid 206, and the outlet 240 is formed in the sidewall 208 of the fluid retaining member 202. The inlet and outlet 238, 240 can each be formed from an opening or port formed in the sidewall, and can optionally include valve 242 for connecting the inlet and/or outlet 238, 240 to an outside fluid source or fluid conduit, and/or for controlling the flow of fluid therethrough.

Referring back to FIG. 1, the container 12 is coupled to a driver mechanism 14 having two syringes 26, 28 mated to a mechanical driver 31. One or both of the syringes 26, 28 can optionally be removable from the driver mechanism 14 to allow one or both of the syringes to be filled with fluid and placed back into the driver mechanism 14. Each syringe 26, 28 includes a barrel 30, 32, and a plunger 34, 36 slidably disposed within the barrel 30, 32. The proximal end 38, 40 of each plunger 34, 36 is mated to the mechanical driver 31, and the distal end 42, 44 of at least one of the barrels 30, 32 is mated to at least one conduit 49 that is coupled to the container 12. In use, the mechanical driver 31 is movable between a first position, in which each plunger 34, 36 is substantially disposed within the barrel 30, 32, and a second position, in which each plunger 34, 36 is substantially extended from the barrel 30, 32.

A person having ordinary skill in the art will appreciate that, while a vertically oriented driver mechanism is illustrated, the driver mechanism can have a variety of configurations. By way of non-limiting example, the driver mechanism can be positioned at an angle, or horizontally, to facilitate use of the device. The driver mechanism can also optionally include a mechanical and/or electrical actuation mechanism for moving the mechanical driver to cause fluid to flow through the system. By way of non-limiting example, the driver mechanism can be mated to a ratchet-style handle or similar mechanism for moving the plunger(s). Other suitable actuation mechanisms include a ratchet adapted to wind the constant force springs, and a worm-gear or simple threading coupled to the plungers and including a knob for actuating the same. A person having ordinary skill in the art will appreciate that virtually any actuation mechanism can be employed with the system according to the present invention. The system can also optionally be manually actuated.

Figure 3:
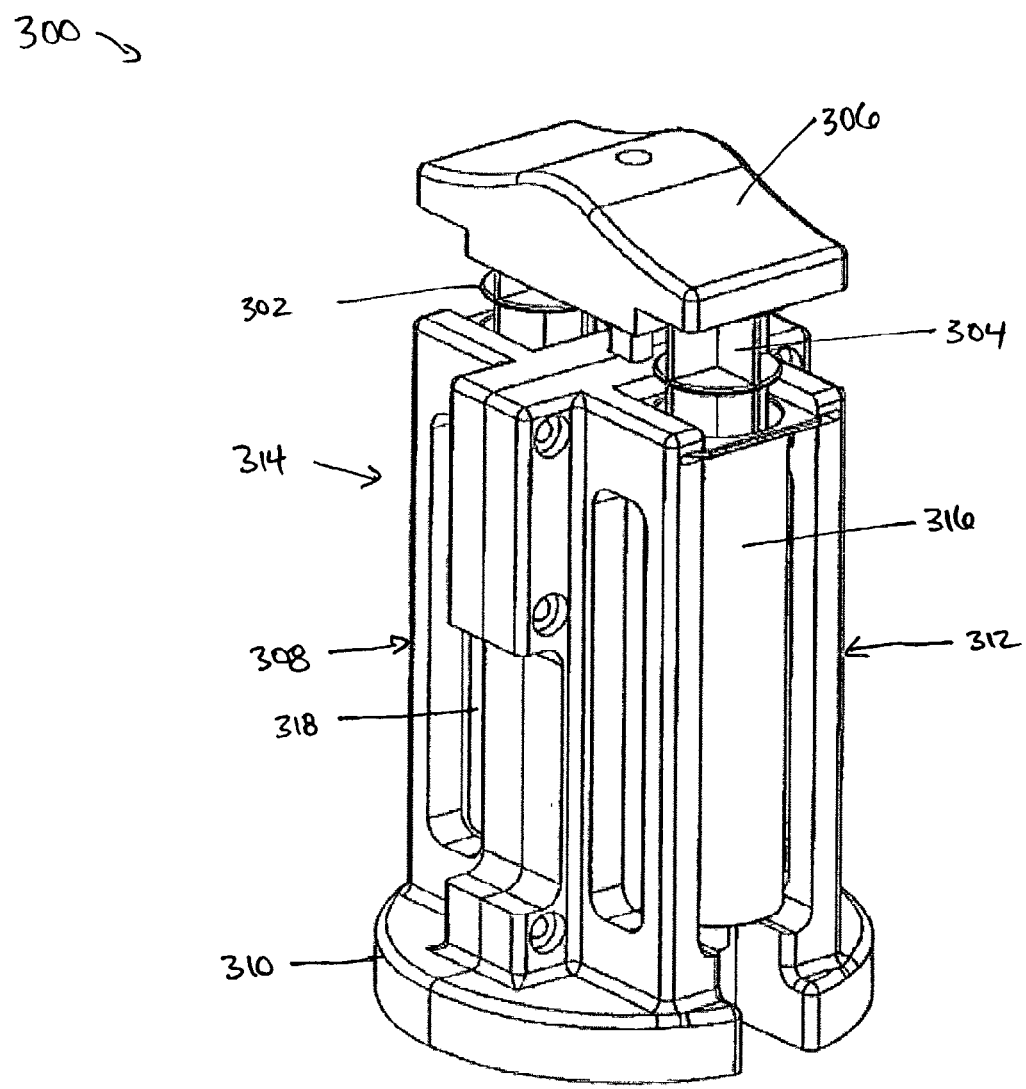
FIG. 3 is a perspective view of one embodiment of a driver mechanism for use the system shown in FIG. 1.

FIG. 3 illustrates an exemplary embodiment of a driver mechanism 300 having two syringes 316, 318 coupled to a mechanical driver 306. The driver mechanism 300 includes a support housing 314 having a base 310, and first and second syringe-holding compartments 308, 312. A mechanical driver 306 is movably connected to the base 310 and syringe-holding compartments 308, 312, and includes an attachment member (not shown) for mating with the plunger 302, 304 of each syringe. In use, the mechanical driver 306 is movable between a first position, as shown, in which the plungers 302, 304 are substantially disposed within the barrel of each syringe 316, 318, and a second position (not shown), in which the plungers 302, 304 are substantially extended or removed from the barrel of each syringe 316, 318. The driver mechanism 300 further includes at least one constant force spring (not shown) that extends between the base 310 and the mechanical driver 306. While a variety of constant force springs can be used, an exemplary constant force spring is the Neg'ator® Spring manufactured by Stock Drive Products/Sterling Instrument. The constant force spring is preferably effective to apply a substantially constant force to the system 10 to drive fluid through the system 10 at a substantially constant flow rate. In an exemplary embodiment, the plunger 302, 304 of each syringe is biased to one of the first and second positions, and preferably to the second position in which the plungers 302, 304 are substantially extended from the barrel of each syringe 316, 318. In use, the driver mechanism 300 is effective to create a constant pressure differential in the system 10 to transport fluid through the system. In a preferred embodiment, a negative pressure differential drives fluid through the container 12, and a positive pressure differential drives fluid through the recycling conduit 48 back to the reservoir in the container 12.

Referring back to FIG. 1, the driver mechanism 14 can be coupled with the container 12 via one or more conduits. As shown, the container 12 includes a recycle conduit having a first portion 46 extending from the outlet 20 of the container to a connector 50, and a second portion extending from the connector 50 to the inlet 22 of the container 12. A withdrawal conduit 49 extends from the distal end 42 of the barrel 30 of syringe 26 to the connector 50 to couple with the portions 46, 48 of the recycle conduit.

Conduit 49 can also optionally extend to and mate with the distal end 44 of syringe 28, depending on the amount of fluid desired to be circulated through the system 10. The use of one or both syringes 26, 28 can vary to permit two different flow rate settings for a volume V of fluid. In an exemplary embodiment, a common stopcock manifold 56 is disposed in conduit 49 between the first and second syringes 26, 28. When the stopcock 56 is in the closed position, the second syringe 28 will vent to the outside air, and thus only one-half the volume V of fluid will be drawn through the system. When the stopcock 56 is in the open position, both syringes 26, 28 are used to draw fluid through the system, and thus the entire volume V is drawn through the system 10. A person having ordinary skill in the art will appreciate that the configuration of the syringes 26, 28 can vary, and that the system 10 can include one or more syringes, or similar devices, such as an expandable bellows, for drawing fluid through the system.

The system 10 can also optionally include one or more mechanisms for controlling the direction of fluid flow. By way of non-limiting example, one or more one-way or dual-check valves can be provided for controlling the direction of fluid flow. Preferably, connector 50 is one-way valve that prevents fluid from flowing into conduit 46, and directs fluid from conduit 46, or from the syringes 26, 28, to the inlet 22 of the container 12 via recycle conduit portion 48. Other one-way valves 52, 54 can optionally be disposed between the conduit 46 and the distal end 42, 44 of each syringe 26, 28.

FIGS. 4A–5B illustrate another embodiment of a system 100 for preparing an implantable substrate, such as a bone graft, in which all of the components are disposed within a housing to form an integral unit. As shown in the exploded view of the system in FIG. 4D, the system 100 includes a housing having a front portion 116, a rear portion 146, and an optional stand 148, a driver mechanism 114 disposed between the front and rear housings 116, 146, and a container 112 coupled to the driver mechanism 114 and positioned within a portion of the front housing 116.

Figure 4A:
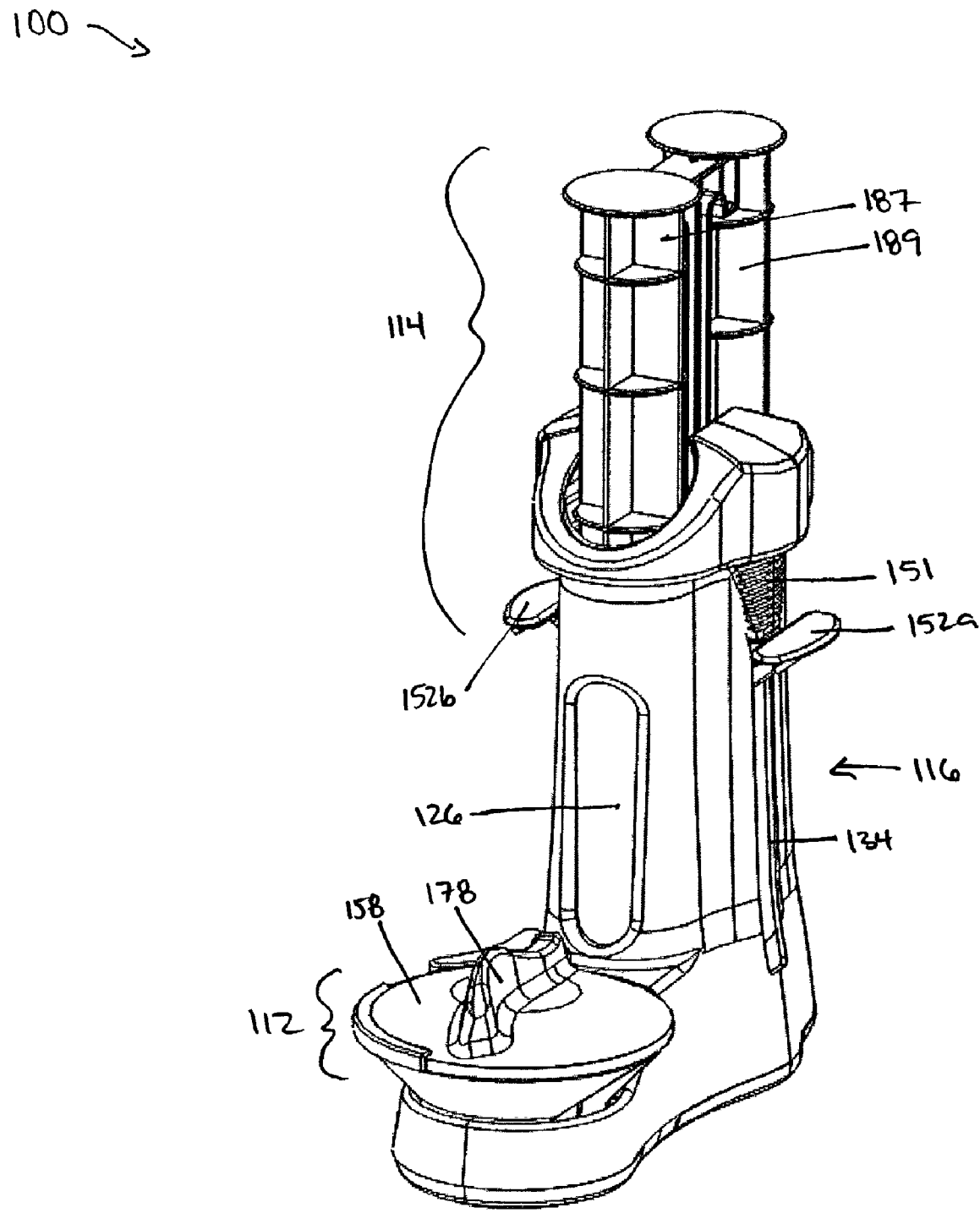
FIG. 4A is a perspective view of another embodiment of a system according to the present invention.
Figure 4B:
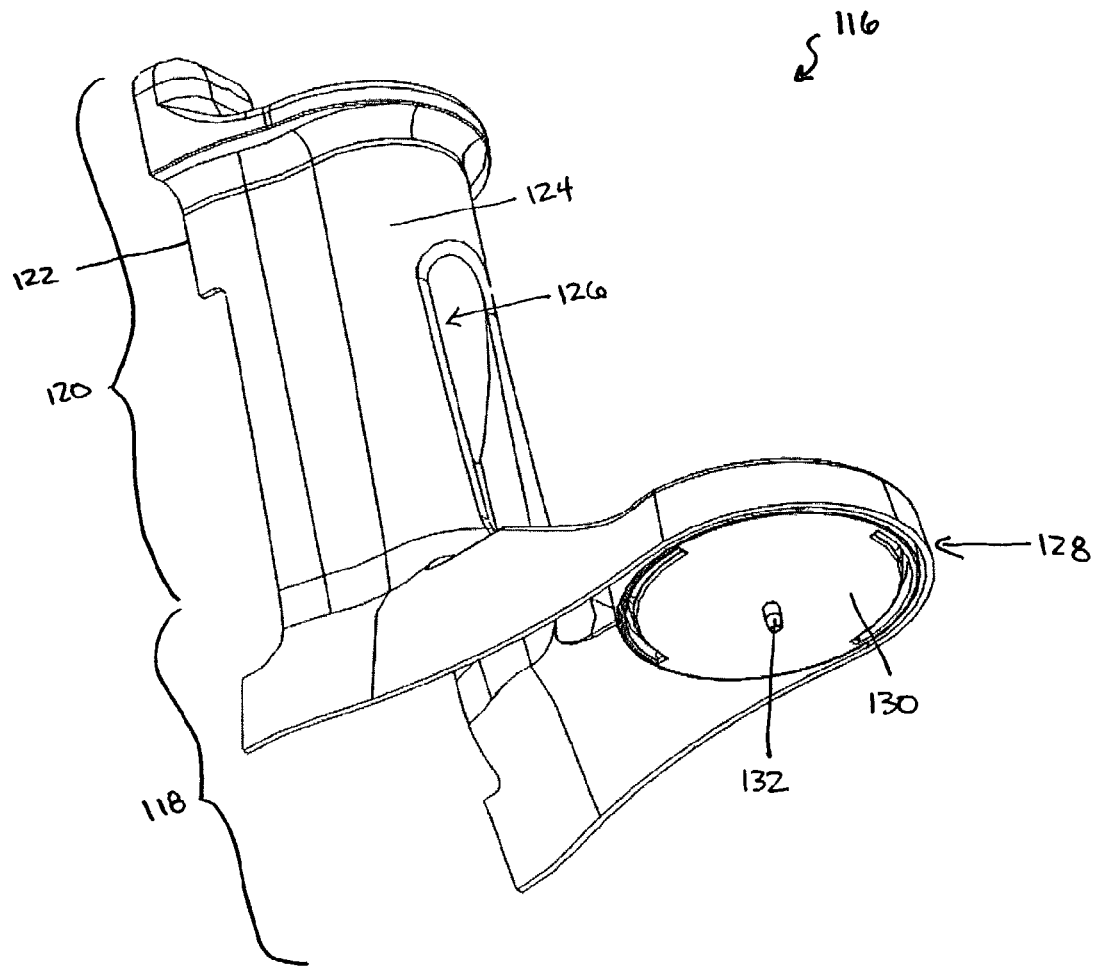
FIG. 4B is a perspective view of the housing of the system shown in FIG. 4A.
Figure 4C:
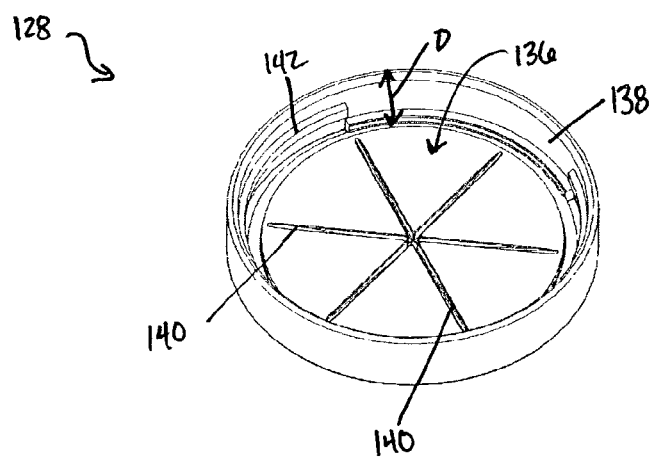
FIG. 4C is a perspective view of one embodiment of the bowl-shaped member of the housing shown in FIGS. 4A and 4B.
Figure 4D:
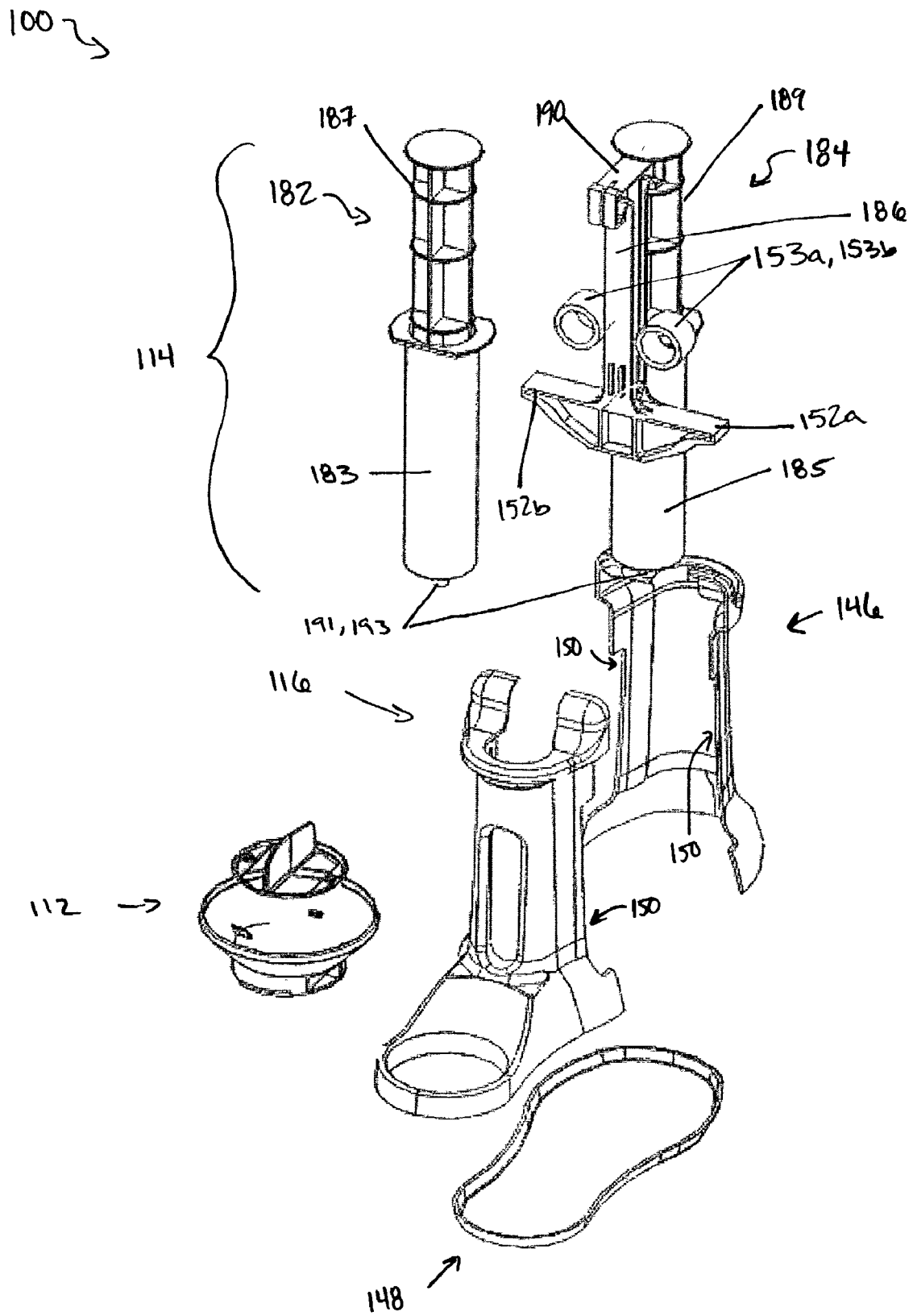
FIG. 4D is an exploded view of the system shown in FIG. 4A.

The housing can have a variety of configurations, and can have virtually any shape and size. A person having ordinary skill in the art will appreciate that FIGS. 4A, 4B and 4D illustrate only one embodiment of the housing. As shown in FIG. 4B, the front portion of the housing 116 includes a base portion 118 and an upright portion 120. While the shape of the housing 116 can vary, the housing 116 is shown having a boot-like shape wherein the upright portion 120 extends in a direction transverse to the base portion 118. The upright portion 120 of the housing 116 includes an open back 122 for receiving the driver mechanism 114 and, when mated to the rear housing 146, has a substantially cylindrical, hollow shape that defines a driver mechanism compartment 124. The upright portion 120 can include at least one window 126 formed therein for viewing a syringe mated to the driver mechanism 114. The window 126 can be formed from a cut-out in the housing 116, and can optionally include a clear, transparent material extending there across.

Figure 5A:
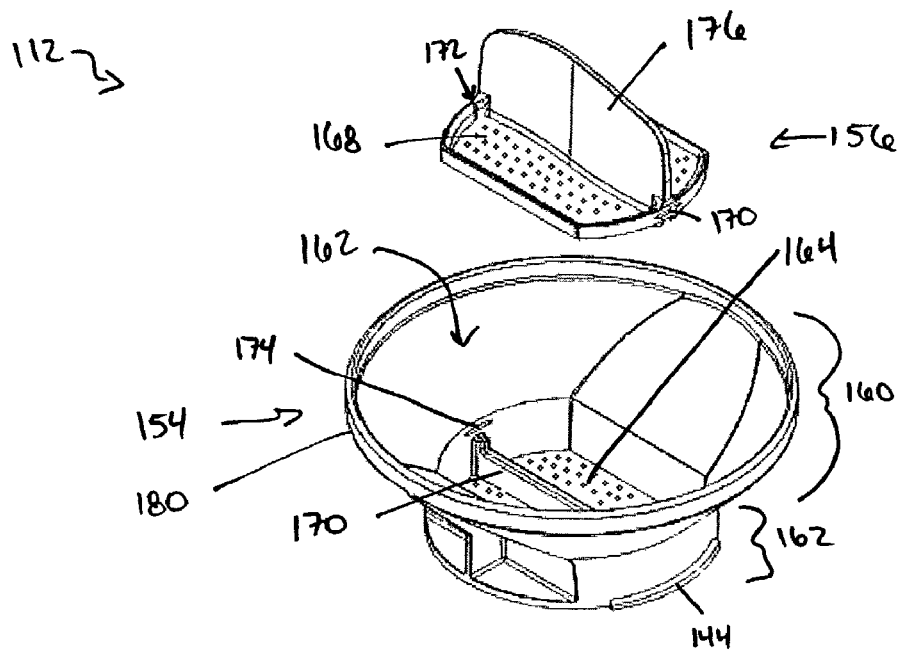
FIGS. 5A and 5B are perspective views of one embodiment of a container for use with the system shown in FIG. 4A.
Figure 5B:
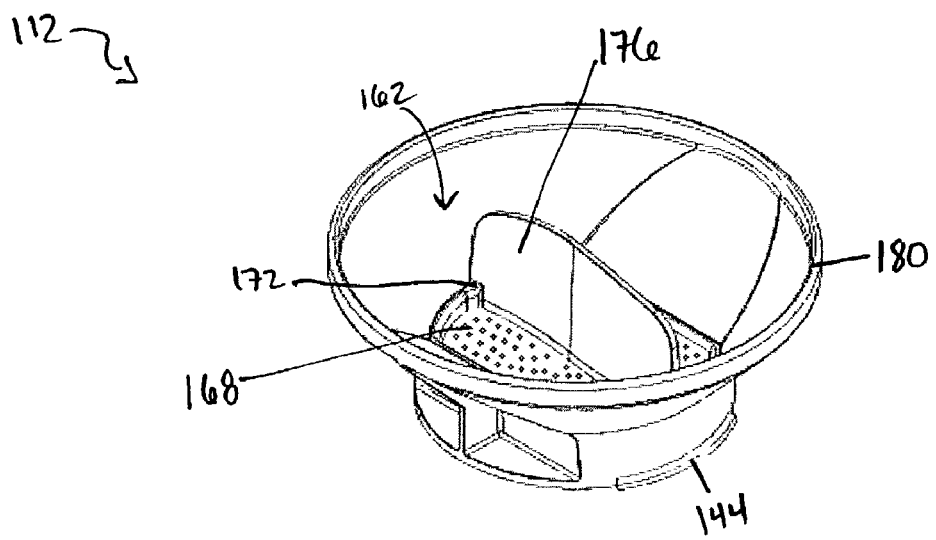

The base 118 of the housing 116, which extends in a direction transverse to the upright portion 120, serves as a support for the upright portion 120 and driver mechanism 114, and includes bowl-shaped member 128 having a recess 136 for seating the container 112. The recess 136 in the bowl-shaped member 128 should have an outer portion 138 or rim sufficient to fit snuggly around the perimeter of the container 112, and should have a depth D large enough to receive fluid flow from the container 112. The outer portion 138 of the bowl-shaped member 128 can include a mating element, such as threads 142, for mating with corresponding threads 144 formed on the outside of the container 112 (FIGS. 5A and 5B). While the bowl-shaped member 128 can have any shape and size, the recess 136 preferably has a funnel-shape and includes one or more volume-reducing ribs or grooves 140. The ribs or grooves 140 can have any shape and size, but preferably have a low profile so as to not interfere with the flow of fluid through the system 100. The rib or grooves 140 are effective to reduce the volume of fluid that can be received by the bowl-shaped member 128. This is particularly advantageous in that the small volume of the bowl-shaped member 128 will only allow a small portion of fluid to pass through the container 112 without being driven through using the driver mechanism 114. The bottom 130 of the bowl-shaped member 128 preferably includes a port 132 for draining fluid from the bowl-shaped member 128, and a recycle conduit (not shown) preferably extends from the port 132 to an inlet in the container 112.

The rear housing 146 is similar in shape to the upright portion 120 of the front housing 116 and, when mated to the front housing 116, is effective to enclose driver mechanism 114 within the housing. At least one of the rear and front housings 116, 146 preferably include a longitudinal detent 150 which forms a longitudinal slot 134 in the housing for slidably receiving a trigger mechanism 152 effective to activate the driver mechanism 114.

The housing can also optionally include a tray 148 for seating the front and rear housings 116, 146 and enclosing the system 100. The tray 148 is preferably a solid, substantially planar member that contours the shape of both the front and rear housings 116, 146 such that the tray 148 fits around or within the bottom of each housing portion 116, 146.

The driver mechanism 114, which is disposed within the housing, is similar to driver mechanism 300 shown in FIG. 3 and includes one or more syringes 182, 184 mated to a mechanical driver 186. As shown in FIG. 4D, each syringe 182, 184 includes a barrel 183, 185, and a plunger 187, 189 slidably disposed within the barrel 183, 185 for applying a force to fluid disposed within the system 100. A portion of each plunger 187, 189 is removably mated to the mechanical driver 186, preferably via a crossbar 190 formed on the proximal end of the driver 186. A variety of mating techniques can be used to connect the plungers 187, 189 to the crossbar 190, such as a snap-fit engagement, a threaded engagement, and other similar mechanical engagements. The distal end 191, 193 of each syringe barrel 183, 185 mates with a conduit (not shown) which is in communication with the port 132 in the bowl-shaped member 128 of the housing 116. In use, movement of the plungers 187, 189 from a proximal-most position, as shown in FIG. 4A, to a distal-most position, in which the plungers 187, 189 are substantially disposed within the barrels 183, 185, creates a suction force in the system 100 that causes fluid to flow through the container 112.

The mechanical driver 114 can be actuated using a variety of techniques, including both mechanical and electrical techniques. As shown in FIG. 4D, the mechanical driver 186 is mated to two constant force springs 153a, 153b which are effective to apply a substantially constant force to the driver 186, and thereby control the flow of fluid through the system. A person having ordinary skill in the art will appreciate that devices other than constant force springs can be used to move the driver mechanism 186. By way of non-limiting example, FIG. 4A illustrates a constant force spring 151 mated to the driver 186. Referring back to FIG. 4D, the driver 186 is preferably biased to the proximal position. In this position, the constant force springs 153a, 153b are fully retracted, as shown. The driver 186 can be actuated by moving the driver 186 in a distal direction, thereby extending the springs 153a, 153b and positioning the plungers 187, 189 so that they are substantially disposed within the barrels 183, 185. The springs 153a, 153b, which are biased to the closed position, will apply a force to the driver 186 to move the driver proximally, and thereby move the syringe plungers 187, 189. The driver 186 can include one or more trigger mechanisms 152a, 152b for moving the driver 186 between the extended and retracted positions. The trigger mechanisms 152a, 152b preferably extend outward through the slots 134 formed by the detents 150 in the front and rear housing 116, 146.

Referring back to FIG. 4A, the system 100 further includes a container 112 disposed within the bowl-shaped member 128 of the housing 116. An exemplary embodiment of a container 112, which is disposed within the bowl-shaped member 128 of the housing 116, is shown in more detail in FIGS. 5A–5B. The container 112 is somewhat similar to container 200 and includes a fluid retaining member 154, a first lid 156 disposed within the fluid retaining member 154, and a second lid or cover 158 (FIG. 4A) removably disposed on one end of the fluid retaining member 154. The fluid retaining member 154 can have virtually any shape, such as square, cylindrical, etc., and can have any size. As shown, the fluid retaining member 154 has funnel-shaped proximal portion 160 and a substantially cylindrical distal portion 162, each of which defines a substantially hollow interior 162 extending therethrough. The distal portion 162 can include a mating element, such as threads 144, formed on an outer surface thereof to mate the container 112 with the bowl-shaped member 128 in the housing 116. The hollow interior 162 preferably has a size and shape adapted to receive an implantable substrate, or a structure holding an implantable substrate. Preferably, a first porous member 164, such as a screen or netting, extends across the distal portion 162 and forms the base of the container 112. A divider 170 can be provided for positioning the first lid 156 at a distance apart from the first porous member 164. Alternatively, or in addition, the distal portion 162 can have a shape adapted to position the first lid 156 at a distance apart from the first porous member 164.

The first lid 156 can also have a variety of configurations, but should be adapted to retain an implantable substrate between the first porous member 164 and the lid 156, and to allow fluid to flow therethrough. As shown in FIG. 5A, the first lid 156 has a shape that is sized to fit within the hollow interior 162 of the fluid retaining member 154. A second porous member 168 extends across at least a portion of the first lid 156 for allowing fluid to flow through the lid 156 while preventing passage of the implantable substrate that is contained between the first and second porous members 164, 168.

A person having ordinary skill in the art will appreciate that the first and second porous members 164, 168 can be formed from a variety of materials including, for example, mesh or woven screens, netting, and laser etched, die cut, or injection molded holes formed in a removable insert. Alternatively, the porous members 164, 168 can be integrally formed with the first lid 156 and fluid retaining member 154. The pores or apertures formed in each of the porous members can have any shape and size, but preferably have a size between about 175 and 600 microns.

The first lid 156 can further include one or more mating elements for mating the lid 156 to the fluid retaining member 154. By way of non-limiting example, FIG. 5A illustrates first and second protruding members 170, 172 positioned on opposed sides of the first lid 156. The protruding members 170, 172 are design to snap-fit into corresponding detents 174 (only one of which is shown in FIG. 5A) formed in the fluid retaining member 154. A person having ordinary skill in the art will appreciate that a variety of mating techniques can be used to mate the first lid 156 to the fluid retaining member 154 including, for example, a snap-fit engagement, a magnetic engagement, an interference fit, and a threaded engagement. The first lid 156 can also optionally include a grasping member or handle 176 mated thereto to facilitate placement of the first lid 156 in the fluid retaining member 154. The handle 176 can have any shape and size, but should have a low profile so as to not interfere with the flow of fluid through the lid 156.

The container 112 also includes a second lid 158, shown in FIG. 4A, that is integrally formed with or removably matable with the proximal portion 160 of the fluid retaining member 154. The lid 158 can have any shape and size, but should be sized to seal the hollow interior 162 of the fluid retaining member 112. The lid 158 preferably has a substantially cylindrical shape and includes a handle 178 to facilitate grasping of the lid 158. An inlet port is preferably formed in the lid 158 to deliver fluid from the driver mechanism 114 to the container 112. The lid 158 can mate with a rim 180 formed on the proximal portion 160 of the fluid retaining member 112, or alternatively the lid 158 can extend around the proximal portion 160 of the fluid retaining member 112. A variety of mating techniques can be used to mate the lid 158 to the fluid retaining member 112 including, for example, a snap-fit engagement, a magnetic engagement, an interference fit, and a threaded engagement. In an exemplary embodiment, the lid 158 is hinged to the housing 116 and snaps onto the container 112.

Figure 4E:
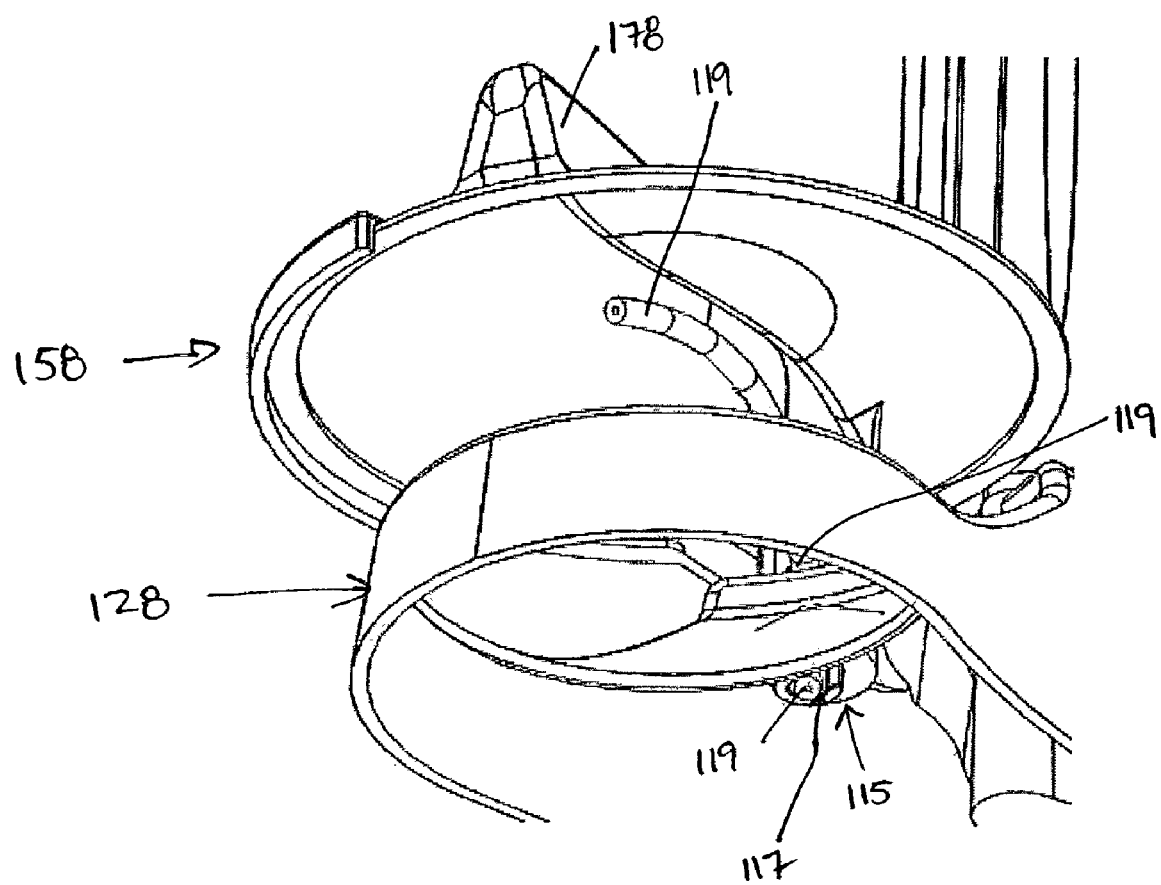
FIG. 4E is a partial cut-away view of a the lid and bowl-shaped member of the housing shown in FIG. 4A.

An exemplary embodiment of a hinge 115 is shown in FIG. 4E, which illustrates a partial cut-away view of the bowl-shaped member 128 of housing 116, and the second lid member 158 mated thereto. The hinge 115 includes an inner lumen 117 extending therethrough for receiving a portion of a fluid recycling conduit 119 that extends from the outlet 132 in the bowl-shaped member 128 (FIG. 4B), through the inlet port in the lid 158, and into the container 112. In use, the second lid 158 (FIG. 4A) is movable between a closed position, and an open position in which the hinge 115 is effective to pinch the fluid recycling conduit 119 that extends through the hinge 115 to prevent fluid from entering the container 112 via the conduit 119. In the illustrated embodiment, the lid 158 swivels to the side with respect the container 112 and the housing 116.

Figure 6:
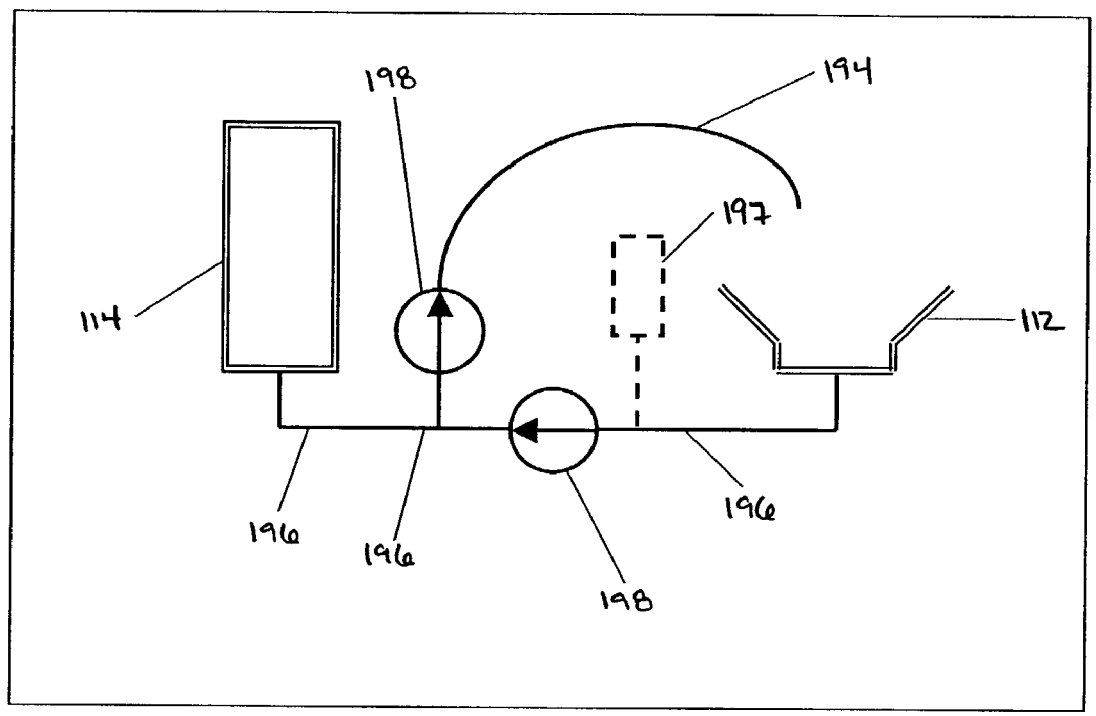
FIG. 6 is a chart illustrating the flow of fluid through the system shown in FIG. 4A.

FIG. 6 is a schematic representation of an exemplary embodiment of the flow of fluid through the system 100 shown in FIG. 4A. As shown, fluid is first placed into the container 112, either by opening or removing the lid 158 to expose the container 112, and injecting fluid through an inlet port in the container 112. While not preferred, fluid can be disposed within one of the syringes in the driver mechanism. Due to the porous nature of the porous members 164, 168 in the lid 156 and the fluid retaining member 154, some fluid will automatically flow into the bowl-shaped member 128 of the housing 116 under the influence of gravity. Accordingly, as previously stated, it is desirable to have a bowl-shaped member 128 having a small volume to prevent a significant amount of fluid from flowing through the implantable substrate prior to actuating the driver mechanism 114. Once the fluid is placed into the container, the lid is closed. The driver mechanism 114 is then actuated by applying a downward force to the plungers 183, 185. This causes any air in the system to be forced out of the syringe barrels 183, 185 and into a recycle conduit 194, which is coupled to the inlet of the container 112. The springs 153*a*, 153*b* then apply a force to the driver mechanism 186 to pull the plungers 187, 189 in a proximal direction with respect to the syringe barrels 183, 185. This draws fluid through the bowl-shaped member 128 into syringe barrel 183 via a conduit 196 extending from the outlet 132 in the bowl-shaped member 128 to the distal end 191 of syringe barrel 183. The driver mechanism 114 is then actuated again by placing a downward force on the triggers 152*a*, 152*b* to force the plungers 187, 189 down into the barrels 183, 185. This forces fluid out of each syringe 182, 184 and back into the inlet in the cartridge 112. The driver is then actuated again to draw fluid in the inlet on the container 112 through the container 112 and the implantable substrate disposed therein. At least one one-way valve 198 is disposed in the conduit 196 extending between the syringe barrels 183, 185 and the outlet 132 of the bowl-shaped member 128 to prevent fluid from flowing into the outlet 132. The one-way valve(s) 198 thus direct fluid from the syringe barrels 183, 185 to the container 112 via the recycle conduit 194, and from the outlet of the container 112 to the syringe barrels 183, 185, while preventing fluid from flowing from the syringe barrels 183, 185 to the outlet of the container 112. The process of directing fluid through the container 112 can be repeated several times, as desired.

The present invention also provides methods for controlling the rate of fluid flow through the system. By way of non-limiting example, the system can include conduits formed from micro-bore tubing to control the rate of fluid flow. In an exemplary embodiment, the conduit extending from the distal end 44 of second syringe 28 is open to an outside air source and has a very small diameter to control the rate of movement of the plunger 36 within the barrel 32. Since the second plunger 28 is mated to the first plunger 26, via mechanical driver 31, the controlled movement of the second plunger 28 will control the rate of movement of the first plunger 28, and will thereby control the flow of fluid through the system. Alternatively, or in addition, the syringes themselves can be adapted to control the fluid flow rate. For example, the proximal portion of one or both syringe barrels 30, 32 can include a one-way valve which allows air to flow into the barrel 30, 32 during compression of the plunger 34, 36, and limits or prevents air from flowing out of the barrel 30, 32 when the plunger 34, 36 is retracted from the barrel 30, 32. In this embodiment, the proximal end of each barrel 30, 32 would need to be sealed, for example, using an o-ring. In another embodiment, the container can be modified to control the rate of fluid flow through the system. By way of non-limiting example, the container, which forms a sealed chamber, can include one or more bleeder valves for regulating air flow. The valve is preferably a one-way valve formed in the lid of the container and effective to allow air to be pushed out of the chamber in the container, but to prevent air from being suctioned into the chamber in the container. The container lid can also include one or more pores for letting air flow into the chamber. The combination of the outlet valve and the inlet pores is effective to regulate the flow of fluid through the system.

FIGS. 7A–7C illustrate yet another embodiment of the present invention. As shown, system 500 is similar to systems 10 and 100 shown in FIGS. 1 and 4A except that, instead of using syringes to force fluid through the system, an expandable bellows 502 is provided. As shown in FIG. 7A, the bellows 502 is disposed within a housing 504 and is mated to a spring 506. A handle or plunger 508 is also provided for actuating the bellows 502. The bellows 502 and the plunger 508 form the driver mechanism of system 500. In use, a downward force applied to the handle 508 moves the bellows 502 to a retracted position, shown in FIG. 7A, and an upward force applied to the handle 508 moves the bellows 502 to a fully expanded position, shown in FIG. 7B.

The housing 504 which retains the bellows is mated to a fluid retaining member 510, which is preferably positioned distal of the housing 504. The fluid retaining member 510 can have any shape and size, and preferably includes first and second compartments 512, 514. The first compartment 512, e.g., the container, is adapted to retain an implantable substrate, such as a bone graft 516. An implantable substrate can be directly disposed within the first compartment 512, or a separate container 516 (FIGS. 8A and 8B) can be removably disposed within the first compartment 512 for holding the implantable substrate. The container 516 will be described in more detail with respect to FIGS. 8A and 8B. The second compartment 514 of the fluid retaining member 510 forms the reservoir and is merely adapted to hold a volume of fluid. The first and second compartments 512, 514 can be separated by a porous, substantially planar surface 518 that extends therebetween, or alternatively can be separated by the container 516.

In use, fluid is disposed within the second compartment 514, as shown in FIG. 7A and the handle 508 is retracted from within the housing 504 to draw fluid from the compartment 514 into the bellows 502, as shown in FIG. 7B. A conduit 520 extends between the second compartment 514 and the bellows 502 to allow fluid to flow therethrough. Once the bellows 502 is filled with fluid and is fully expanded, the spring 506 applies a force to the bellows 502 to move the bellows 502 back to the retracted position. The handle 508 can optionally be used to retract the bellows 502. This causes the fluid disposed within the bellows 502 to be pushed into the first compartment 512 and through the graft 516, whereby the fluid is collected in the second compartment 514, as shown in FIG. 7C. A conduit 522 extends from the bellows to the first compartment 512 to allow fluid to flow therethrough. The conduits 520, 522 can include one-way valves for controlling the direction of fluid flow. Preferably, conduit 522 includes a valve permits fluid flow only in a direction from the bellows to the first compartment 512, and conduit 520 includes a valve that permits fluid flow only in a direction from the second compartment 514 to the bellows 502. An exemplary embodiment of a flow-control device is described in more detail below with respect to FIGS. 10A–10C.

Figure 8A:
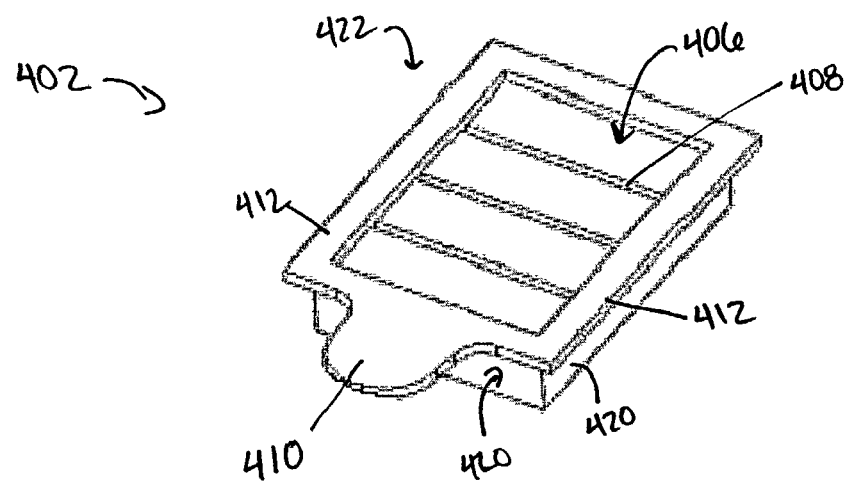
FIGS. 8A and 8B are perspective views of one embodiment of a container for use with the system shown in FIGS. 7A–7C.
Figure 8B:
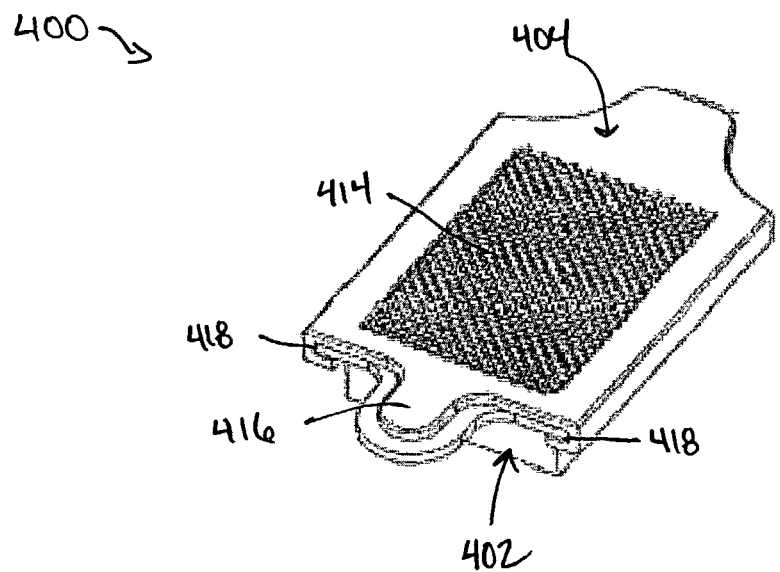

One embodiment of a container 400 for use with system 500 is shown in FIG. 8B. The container 400 includes a tray member 402 and a lid member 404. The tray member 402 is shown in FIG. 8A and has a substantially rectangular shape and a hollow interior formed therein. The tray 402 preferably includes a distal surface 406, an open proximal end 422, and four sidewalls 420 extending in a direction transverse to the distal surface 406. The open proximal end 422 preferably includes a rim 412 extending around the sidewalls for sliding into a corresponding grooves 418 formed in the lid 404. The distal surface 406 of the tray 402 is preferably adapted to allow fluid to flow therethrough. By way of non-limiting example, the bottom surface 406 can include one or more slots 408 extending across the surface 406. Alternatively, the surface 406 can be formed from a permeable or porous material. The lid 404, which is shown in FIG. 8B, also preferably includes a porous surface 414 to allow fluid to flow through the container 400. The lid 404 is preferably a substantially planar member having elongate grooves 418 extending along opposed edges thereof for mating with the tray 402. The lid 404 and the tray 402 can optionally include tabs 416, 410 to facilitate proper mating of the two members. The tabs 416, 410 can be design to engage one another upon insertion of the lid 404 onto the tray 402. In use, the container 400 is designed to retain a graft in the hollow interior of the tray 402, and is effective to enable fluid to flow therethrough.

Figure 9:
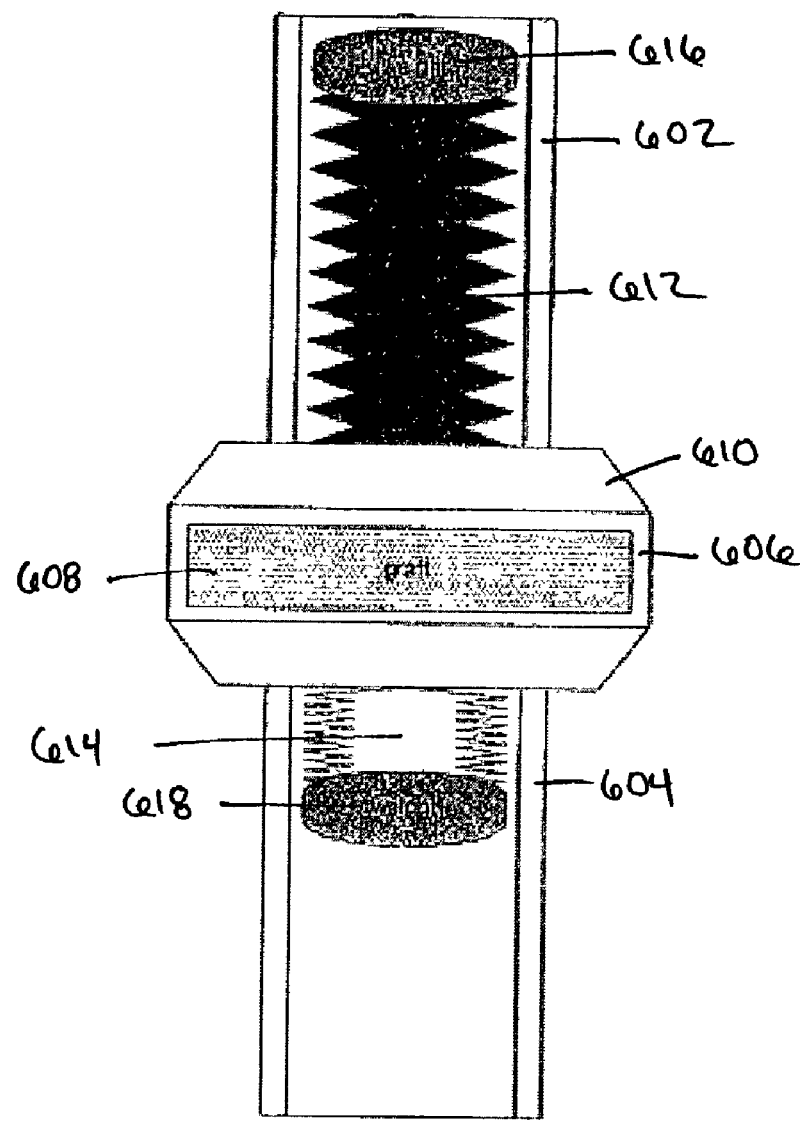
FIG. 9 is a perspective view of yet another embodiment of a system according to the present invention.

FIG. 9 illustrates yet another embodiment of the present invention in which the system is reversible to allow fluid to flow through an implantable substrate in two directions. As shown, the system 600 includes first and second opposed housings 602, 604. A container 606 is disposed between and coupled to the housings 602, 604. The container 606 is adapted to hold an implantable substrate, such as a graft 608, and can be removably disposed within a separate housing 610 mating the first and second housings 602, 604. The first and second housings 602, 604 each include an expandable bellows 612, 614, and a driver mechanism, such as a mass 616, 618, for apply force to the bellows 612, 614 to move the bellows 612, 614 between the expanded and retracted states.

In use, the system 600 is positioned in a first direction, as shown, in which bellows 612 is in the fully expanded state and has fluid disposed therein, and opposed bellows 614 is in the unexpanded position. The mass 616 will apply a force to the bellows 612 to move the bellows 612 from the expanded state to the unexpanded state, thereby causing fluid to be forced out of the bellows 612 and through the graft 608, preferably at a controlled rate. As bellows 612 moves to the unexpanded state, and fluid flows through the graft 608, bellows 614 moves to the expanded state and collects fluid pushed through the graft 608. The system 600 can then be turned over to cause mass 618 to apply a force to bellows 614 to pass the fluid through the graft again. The system can optionally include a flow-control device for controlling the rate of fluid flow.

Figure 10A:
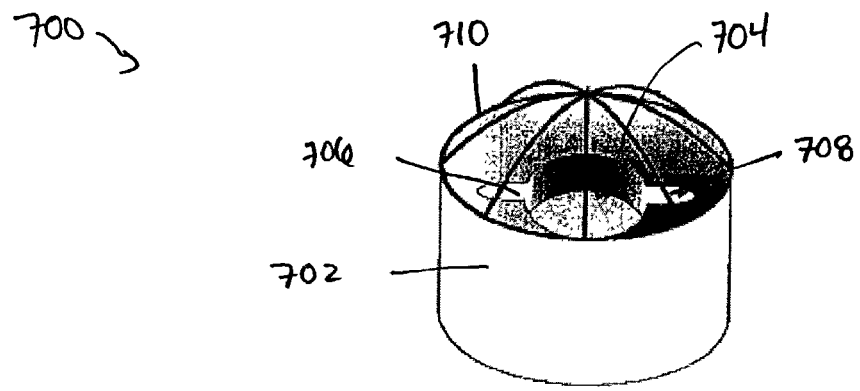
FIG. 10A is a perspective view of one embodiment of a valve for use with a system according to the present invention.
Figure 10B:
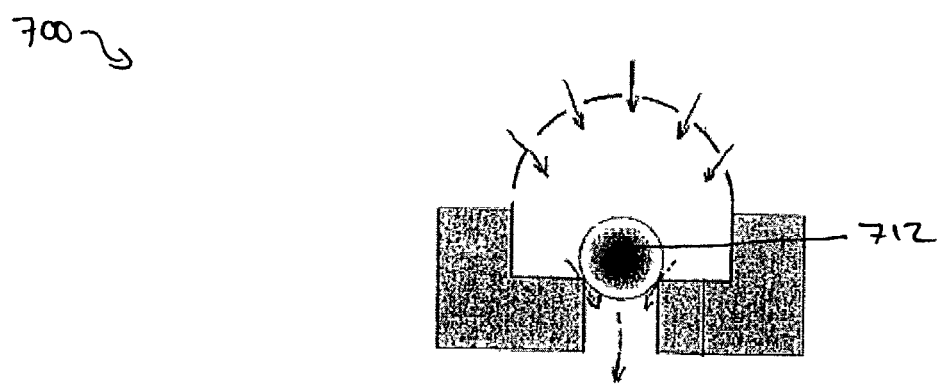
FIGS. 10B and 10C are functional diagrams showing use of the valve of FIG. 10A.
Figure 10C:
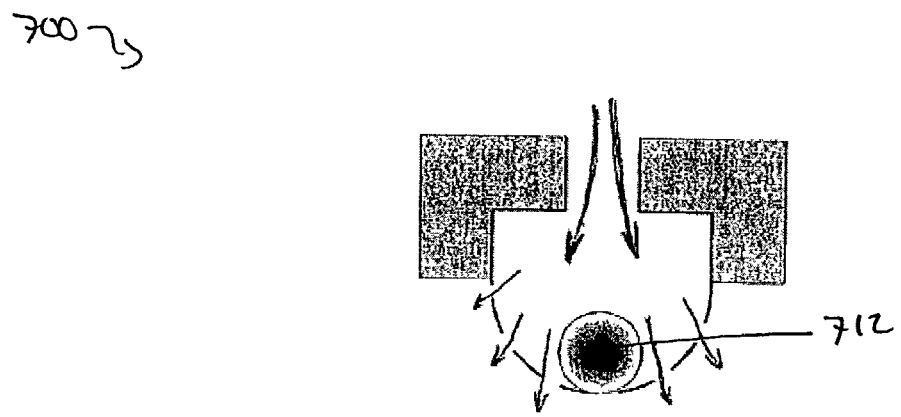

FIGS. 10A–10C illustrate an exemplary embodiment of a flow-control device 700 for use with the systems of the present invention. The flow-control device 700 is in the form of a substantially elongate, cylindrical ball-valve seat 702 having an opening 704 extending therethrough. The opening 704 is substantially circular and includes two notched portions 706, 708 positioned on opposed sides of the opening 704. A cage 710 surrounds one end of the cylindrical ball-valve seat 702, and is effective to retain a ball 712 therein. In use, as shown in FIG. 10B, the ball 712 sits within the opening 704. Fluid flowing in the direction indicated will be prevented from flowing through the opening 704 due to the ball, but will be allowed to flow through the notched portions 706, 708. As a result, the rate of fluid flow through the device 700 will be controlled. FIG. 10C illustrates the effect of fluid flow in the opposite direction. In this position, fluid pushed the ball away from the opening, thereby decreasing the flow resistance through the valve seat 700. This allows a substantially free flow of fluid therethrough.

The systems according to the present invention can also be modified to enable a second fluid, such as a clotting solution, to be passed through an implantable substrate simultaneously with the first fluid, e.g., bone marrow. FIG. 6, for example, illustrates a valve 197 connected to the conduit 196 for injecting a second fluid into the system. The valve 197 can have any configuration, but is preferably a needleless valve 197. The position of the valve 197 allows the second fluid to be injected into the system and mixed with the first fluid in the syringe 114 prior to directing the mixture of fluids through the container 112. In an alternative embodiment (not shown), one of the two syringes of systems 10 and 100 shown in FIGS. 1 and 4A can be filled with a second fluid for selectively mixing with the first fluid disposed in the system. A stopcock positioned distal of the syringe containing the second fluid can be used to control the amount of fluid injected into the system.

In an exemplary embodiment, valve 197 is a luer-activated check valve, or needleless valve. A syringe containing a clot-inducing mixture, such as thrombin and calcium, is connected to the valve 197 as a last step in using the device. The mixture is preferably directed through the system in a reverse direction, such that the mixture flows up from the bowl-shaped member 132 and through the implantable substrate. In an exemplary embodiment, the valve 197 is used with the system 100 shown in FIG. 4A. The clotting mixture is preferably injected into the system 100 when the lid 158 is in the open position whereby the hinge 115 (FIG. 4E) pinches the fluid recycling conduit 119 that extends through the hinge 115 to prevent fluid from entering the container 112 via the inlet. As a result of the closed recycling conduit 119, the mixture is forced to flow into the bowl-shaped member 132 and up through the implantable substrate disposed in the container 112.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for preparing a bone graft for implantation, comprising:
   a container defining a reservoir and having an inlet and an outlet;
   a fluid permeable basket disposed within the container and capable of retaining a porous, biocompatible, implantable substrate, the basket comprising a tray-like device having opposed fluid permeable porous members that comprise a porous bottom surface and a porous top surface; and
   a driver mechanism coupled to the container and the reservoir, the driver mechanism being effective to subject any fluid within the reservoir to a constant force so as to induce a selected, controlled flow rate of the fluid through the container.

2. The system of claim 1, further comprising a fluid recycling conduit extending between the outlet of the container and the inlet of the container to recirculate fluid in the reservoir.

3. The system of claim 2, wherein the fluid recycling conduit includes a one-way check valve to prevent any fluid from entering the container through the outlet thereof.

4. The system of claim 2, further comprising a lid member adapted to seal the container.

5. The system of claim 4, further comprising a hinge connecting the lid member to the container and including an inner lumen extending therethrough for receiving a portion of the fluid recycling conduit, wherein the lid member is movable between a closed position, in which fluid can flow through the fluid recycling conduit, and an open position in which the hinge pinches the fluid recycling conduit to prevent fluid from flowing therethrough.

6. The system of claim 1, wherein the driver mechanism comprises a syringe effective to create a constant suction force to transport fluid through the container.

7. The system of claim 6, wherein the syringe is coupled to the inlet and the outlet in the container.

8. The system of claim 6, wherein the syringe includes a barrel and a plunger disposed within the barrel, the plunger being coupled to a constant force spring that is effective to retract the plunger from an initial position, in which the plunger is substantially disposed within the barrel, and a final position, in which the plunger is substantially retracted from the barrel.

9. The system of claim 8, wherein the plunger is sealed within a chamber in the barrel, and wherein the barrel includes at least one airflow valve extending into the chamber to control the rate of movement of the plunger within the chamber and thereby control the flow rate of fluid through the system.

10. The system of claim 8, wherein the plunger is biased to a position in which the plunger is substantially retracted from the barrel.

11. The system of claim 1, wherein the driver mechanism comprises a plurality of syringes effective to create a constant suction force to transport the fluid through the container.

12. The system of claim 11, wherein the syringes each include a plunger disposed within a barrel, and wherein the plunger of each syringe is mechanically coupled to effect substantially simultaneous movement thereof.

13. The system of claim 1, wherein the driver mechanism comprises a first syringe having a plunger disposed within a barrel, the first syringe being effective to create a constant suction force to transport the fluid through the container, and wherein the system further includes a second syringe having a plunger disposed within a barrel, the plunger of the second syringe being mechanically coupled to the plunger of the first syringe to effect substantially simultaneous movement of the plungers within the barrels.

14. The system of claim 13, wherein the second syringe is coupled to an air flow conduit effective to limit the movement of the plunger within the barrel, and thereby to control the rate of fluid flow in the system.

15. The system of claim 1, further comprising a collection tank effective to collect fluid from the outlet of the container, and a fluid recycling conduit extending between the collection tank and the inlet of the container.

16. The system of claim 15, further comprising a withdrawal conduit extending between the fluid recycling conduit and the driver mechanism.

17. The system of claim 1, wherein the container is sealable and includes one or more airflow valves formed therein and effective to control the flow rate of fluid through the container.

18. The system of claim 1, wherein the porous bottom surface and the porous top surface are removably disposed within the container.

19. The system of claim 18, wherein the porous bottom surface and the porous top surface are each formed from an implantable, biocompatible material.

20. The system of claim 1, further comprising a fluid disposed within the system, the fluid being selected from the group consisting of bone marrow, blood, platelet rich plasma, placenta, synovial fluid, and amniotic fluid, suspensions containing stem cells, suspensions containing growth factors, suspensions containing proteins, and combinations thereof.

21. The system of claim 1, further comprising a fluid inlet valve in fluid communication with the container and effective to enable fluid to be introduced into the system.

22. The system of claim 21, further comprising a clotting solution introduced into the system through the fluid inlet valve.

23. A container for holding an implantable substrate, comprising:
  a fluid retaining member having a longitudinal axis, a proximal end, a distal end, and at least one fluid impermeable sidewall defining a substantially hollow interior portion;
  a base member mated to and extending in a direction substantially transverse to the longitudinal axis of the fluid retaining member, the base member having at least one porous portion adapted to allow fluid to flow therethrough;
  a first lid member removably disposed within the hollow interior portion of the fluid retaining member, the first lid member extending in a direction substantially parallel to the base member and including a handle and at least one porous portion adapted to allow fluid to flow therethrough; and
  a second lid member removably mated to the proximal end of the fluid retaining member.

24. The container of claim 23, wherein the first lid member is removably mated to the fluid retaining member by a positive mechanical engagement.

25. The container of claim 23, wherein the first lid member includes an attachment mechanism for selectively mating with a corresponding attachment mechanism formed on the fluid retaining member.

26. The container of claim 23, wherein the first lid member is positioned at about a midpoint in the hollow interior portion of the fluid retaining member.

27. The container of claim 23, wherein a portion of the fluid retaining member extending between the proximal end of the fluid retaining member and the first lid member defines a fluid receiving recess.

28. The container of claim 23, further comprising a support member having a recess for removably receiving the fluid retaining member.

29. The container of claim 28, wherein an outer wall of the fluid retaining member adjacent the distal end includes at least one thread formed thereon for mating to at least one corresponding thread formed on an inner surface of the support member.

30. The container of claim 23, wherein the fluid retaining member has a substantially conical shape.

31. The container of claim 30, wherein the proximal end of the fluid retaining member has a diameter greater than a diameter of the distal end of the fluid retaining member, such that the fluid retaining member includes a proximal, outwardly extending annular lip.

32. The container of claim 23, wherein the porous portion on each of the base member and the first lid member is formed from at least one woven screen disposed across a portion thereof.

33. The container of claim 32, wherein the at least one woven screen is insert-molded into each of the base member and the lid member.

34. The container of claim 32, wherein the at least one woven screen includes pores having a size between about 175 and 600 microns.

35. The container of claim 32, further comprising an implantable bone graft removably disposed between the base member and the first lid member.

36. The container of claim 32, wherein the second lid member is hingedly connected to the fluid retaining member.

37. The container of claim 32, wherein the fluid retaining member includes an inlet positioned upstream of the first lid member and an outlet positioned downstream of the base member, and wherein a fluid recycling conduit extends from the outlet to the inlet.

38. The container of claim 37, further comprising a hinge connecting the second lid member to the fluid retaining member and including an inner lumen extending therethrough for receiving a portion of the fluid recycling conduit, wherein the lid is movable between a closed position, in which fluid can flow through the fluid recycling conduit, and an open position in which the hinge pinches the fluid recycling conduit to prevent fluid from flowing therethrough.

39. The container of claim 23, further comprising a fluid inlet valve formed in the second lid member and in fluid communication with the hollow interior portion, the fluid inlet valve being effective to enable fluid to be introduced into the system.

40. A system for preparing a bone graft for implantation, comprising:
  a reservoir having an inlet and an outlet, the reservoir being capable of selectively retaining a fluid;
  a container coupled to the reservoir and having an inlet and an outlet, the container being fluid permeable, but capable of retaining a porous, biocompatible, implantable substrate; and
  a driver mechanism coupled to the container and the reservoir, the driver mechanism being effective to subject any fluid within the reservoir to a constant force so as to induce a selected, controlled flow rate of the fluid through the container;
  wherein the driver mechanism comprises a syringe effective to create a constant suction force to transport fluid through the container, the syringe including a barrel and a plunger disposed within the barrel, the plunger being coupled to a constant force spring that is effective to retract the plunger from an initial position, in which the plunger is substantially disposed within the barrel, and a final position, in which the plunger is substantially retracted from the barrel.

* * * * *